(12) United States Patent
Deusser et al.

(10) Patent No.: US 6,408,536 B1
(45) Date of Patent: Jun. 25, 2002

(54) PROCESS FOR DRYING PROTEIN CRYSTALS

(75) Inventors: Rolf Deusser, Sulzbach; Peter Kraemer, Eschborn; Horst Thurow, Kelkheim, all of (DE)

(73) Assignee: Aventis Pharma Deutschland GmbH, Frankfurt am Main (DE)

( * ) Notice: Subject to any disclaimer, the term of this patent is extended or adjusted under 35 U.S.C. 154(b) by 0 days.

(21) Appl. No.: 09/482,117

(22) Filed: Jan. 13, 2000

(30) Foreign Application Priority Data

Jan. 27, 1999 (DE) .......................... 199 03 125

(51) Int. Cl.[7] ................................. F26B 5/08
(52) U.S. Cl. ...................... 34/312; 34/311; 34/313; 34/314; 34/315; 34/316; 34/321; 34/322; 34/323; 34/324; 34/325; 34/326; 34/337; 34/338; 34/341; 34/317; 34/328; 34/329
(58) Field of Search .................. 34/311–319, 321–329, 34/58, 337, 338, 341; 494/25

(56) References Cited

U.S. PATENT DOCUMENTS

| | | | | |
|---|---|---|---|---|
| 4,139,637 A | * | 2/1979 | Rouchy | 424/323 |
| 5,163,895 A | * | 11/1992 | Titus | 494/36 |
| 5,234,503 A | * | 8/1993 | Lillard, Jr. et al. | 127/42 |
| 5,526,581 A | * | 6/1996 | Winterson et al. | 34/474 |
| 5,659,971 A | * | 8/1997 | Haleen | 34/166 |
| 5,743,840 A | * | 4/1998 | Carr | 494/13 |
| 6,042,824 A | * | 3/2000 | Khalaf | 424/94.6 |

FOREIGN PATENT DOCUMENTS

| | | | |
|---|---|---|---|
| EP | 0454045 A2 | * | 4/1991 |
| EP | 0622376 A1 | * | 4/1994 |
| WO | 97/44445 | | 11/1997 |

* cited by examiner

*Primary Examiner*—Denise L. Esquivel
*Assistant Examiner*—Mark Shulman
(74) *Attorney, Agent, or Firm*—Heller Ehrman White and McAuliffe

(57) ABSTRACT

The present invention relates to a process for drying protein crystals starting from an aqueous protein crystal suspension, which comprises drying the protein crystal suspension in a centrifugal dryer, where the protein crystals, after they have been filtered off from the protein crystal suspension, are brought into contact with a drying medium which consists of a mixture of water and a nonaqueous solvent which is miscible with water in any ratio and which has a lower vapor pressure than water. In the process, a drying gas which has been moistened with water is advantageously used. The protein crystal suspension is advantageously converted into a fluidized bed for the purpose of drying.

17 Claims, No Drawings

PROCESS FOR DRYING PROTEIN CRYSTALS

BACKGROUND OF THE INVENTION

Proteins are present in many commercially available preparation forms. In particular, proteins are present as the active ingredient in some pharmaceutical medicaments. For the preparation of these preparation forms, it is beneficial to use the proteins in crystalline form. As well as being easier to handle in crystalline form proteins as dry crystals are, more stable than, for example, proteins in dissolved form.

As an example, the preparation of a pharmaceutical preparation containing the hormone insulin as active ingredient, uses the protein insulin in crystalline form. Crystallized insulin is stable, for example, at a temperature of −20° C. over a number of years.

Crystalline forms of proteins having a molecular weight of up to several hundred thousand daltons and peptides having a lower molecular weight are known. The amino acid sequence of the proteins can either be identical to a naturally occurring sequence or it can be changed relative to the natural form. In addition to containing amino acid chains, the proteins can also contain sugar radicals or other ligands as side chains. The proteins may be isolated from natural sources, or the protein may be prepared by genetic engineering or synthetically, or the proteins may be obtained by a combination of these processes.

In aqueous solution, proteins have a three-dimensional structure of greater or lesser complexity which is based on a specific spatial folding of the amino acid chains. The intact structure of a protein is essential for its biological action. During crystallization of the proteins from aqueous solutions, this structure is largely retained. The crystal structure of a protein is predominantly determined by its amino acid sequence. Another factor determining crystal structure is, for example, inclusions of low molecular weight substances, such as, for example, metal ion salts and water molecules. In particular, the presence of a certain amount of intracrystalline water molecules (water of crystallization) is necessary for the stability of the crystal structure of proteins.

For example, insulin crystals require an optimum residual water content (roughly between 1 and 7%). If the crystals are overdried and too low a moisture content is achieved, then the water of crystallization has already been removed from the crystals. As a result, the chemical stability of insulin is adversely affected, resulting, for example, in the formation of higher molecular weight compounds. It is assumed that the higher molecular weight fractions in the insulin are responsible for immunological incompatibility reactions. In the extreme case, insulin can be denatured to the extent that the crystals are no longer soluble in aqueous media. If, on the other hand, crystals with too high a moisture content are obtained upon drying, then there is too much water between the individual crystals. The insulin is partly dissolved in this intercrystalline water. The stability of the dissolved insulin is, however, significantly lower than that of solid forms.

It is known that protein crystals, in particular insulin crystals, can be dried by isolating the crystals from a crystal suspension by filtration and drying the filter cake under reduced pressure at a temperature above 0° C. It is also known that the drying process can be accelerated by replacing the intercrystalline water with ethanol prior to drying. During drying, the crystals are distributed in a thin layer on drying sheets or are agitated on the filter.

In another process, the protein crystals, for example insulin crystals, are frozen as an aqueous suspension at a temperature below 0° C. on drying sheets and then freeze-dried under reduced pressure.

In both processes mentioned, the attainment of neither a defined nor optimal residual moisture content in the dried crystals is adequately ensured. In both processes, the drying process is kinetically controlled to the end and must be terminated at a specific time in order to avoid overdrying. Experience shows that it is difficult to determine the correct point in time to terminate the drying. The resulting moisture content of the crystals depends not only on the thickness of the layer on the drying sheet, but also on the size of the crystals (or their surface area). Since the crystallization process leads to insulin crystals having a size distribution of varying width, the crystals dried in a kinetically controlled process consist of a mixture of dryer small crystals and moister large crystals.

Another disadvantage of these processes is that it is very difficult to automate charging and emptying of the equipment used for drying. Thus, the operation of charging and emptying still largely requires manual work, which harbors the risk of contamination by germs and foreign particles. For example, the currently valid pharmacopeia demand that crystalline insulin for the preparation of pharmaceutical preparations must be low in germs but not germ-free. Therefore a need exists for a process of preparing a protein preparation where the process provides crystals with a uniform water content without the risk of contamination.

SUMMARY OF THE INVENTION

The present invention comprises a process for drying protein crystals starting from an aqueous protein crystal suspension, which comprises drying the protein crystal suspension in a centrifugal dryer.

In one embodiment of the invention the process for drying protein crystals starting from an aqueous protein crystal suspension encompasses filtering off the protein crystals from the aqueous protein crystal suspension, and subsequently bringing the protein crystals into a drying medium which consists of a mixture of water and a nonaqueous solvent which is miscible with water in any ratio and which has a lower vapor pressure than water.

DETAILED DESCRIPTION OF THE INVENTION

The present invention involves a process for preparing a protein preparation which preferably comprises the following steps:

1. Filtering off the crystals from an aqueous suspension.
2. Washing the filter cake.
3. Replacing the wash liquid with a drying medium.
4. Spindrying the filter cake.
5. Detaching the filter cake from the filter and converting it into a fluidized bed.
6. Drying the crystals in the fluidized bed with a stream of moistened nitrogen.
7. Emptying the dried crystals using a nitrogen pressure surge into a flanged container.

Accordingly, the present invention relates to a process for drying protein crystals starting from an aqueous protein crystal suspension, which comprises drying the protein crystal suspension in a centrifugal dryer.

For the drying process described, it is particularly advantageous if the detached filter cake can be converted into a fluidized bed. The experiments, carried out in a commercially available dryer, have shown that if the intercrystalline water was not replaced for one of the drying media described below, it was not possible to generate a fluidized bed; a mixture of crystal aggregates of varying size formed instead, making uniform drying impossible.

Other experiments have shown that by replacing the intercrystalline water with a pure nonaqueous drying medium, e.g. 100% strength ethanol or 100% strength propanol, only the intracrystalline water (water of crystallization) remaining in the protein crystals, is it possible to produce a fluidized bed. However, during the subsequent drying phase, the drying medium could not adequately be removed even after a prolonged drying time. The dried products had a residual content of drying medium of more than 5 %. On the other hand, some of the water of crystallization had already been removed during the drying time.

Surprisingly, it has now been found that by replacing the intercrystalline water with a drying medium which consisted of a mixture of water and a nonaqueous substance, it was possible to avoid the disadvantages mentioned. After replacing the intercrystalline water with one of the drying media described below, it was possible to produce a fluidized bed from the detached filter cake and to dry the crystals satisfactorily. Using moistened drying gas, after a drying time of from about 1 to 4 hours, products were obtained which were free from crystal aggregates and have a residual content of the nonaqueous substances of less than 0. 1%.

Accordingly, the present invention relates to a process for drying protein crystals starting from an aqueous protein crystal suspension, wherein, in particular, the protein crystals, which have been filtered off from the protein crystal suspension, are brought into a drying medium which consists of a mixture of water and a nonaqueous solvent which is miscible with water in any ratio and which has a lower vapor pressure than water. The process according to the invention for drying a protein crystal suspension is advantageously carried out in a centrifugal dryer.

The nonaqueous substances which constitutes part of the suitable drying media have a low vapor pressure at a temperature of about 40° C. (i.e. have a lower vapor pressure than water), are miscible with water in any ratio and are chemically inactive toward proteins under specified conditions. Alcohols, such as, for example, methanol, ethanol, n-propanol and isopropanol, are preferable for this use. Mixtures of alcohols are also suitable.

The proportion of nonaqueous substances in the suitable mixtures with water in the drying medium is from about 10% to about 80% inclusive, preferably from 15% to about 60% inclusive, further preferably from about 20% to about 80% inclusive.

In the drying process described using dry nitrogen as drying gas, the drying process is kinetically controlled to the end, meaning that the disadvantages described above can occur.

Our own experiments using moist nitrogen as the drying gas have shown that the removal of the water from the crystals during the drying phase comes to a standstill and the achieved residual water content in the dried crystals is determined by the water content in the drying gas, i.e. at the end of the drying phase a thermodynamic equilibrium between the water content in the drying gas and the water content in the crystals is established. The residual water content in the dried crystals is therefore independent of their size (or surface area).

In addition, the experiments using dry nitrogen as drying gas have shown that the nonaqueous constituent of the drying medium could not be sufficiently removed, even after a prolonged drying period. The dried products had a residual content of the nonaqueous constituent of more than 1 %.

Surprisingly, it has been found that in a process for drying protein crystals using a drying gas, the residual content of the nonaqueous constituent of the drying medium could be removed except for less than 0.1% if a water containing drying gas is used. The drying process is preferably carried out in a centrifugal dryer. In the process for drying protein crystals, it is preferable if the protein crystals, after having been filtered off from the protein crystal suspension, are brought into a drying medium which consists of a mixture of water and a nonaqueous solvent which is miscible with water in any ratio and which has a lower vapor pressure than water. It is more preferable in the process if the protein crystals, after they have been filtered off from the protein crystal suspension, are converted into a fluidized bed for the purpose of drying.

The inventors' experiments with the drying process described have shown that if a sterile crystal suspension free from foreign particles was used, and wash water, drying medium and drying gas were sterilized by filtration, and the centrifugal dryer was suitably cleaned and sterilized, a dried product was obtained which was both germ-free and free from foreign particles.

The process of the present invention is particularly suitable for drying crystals of animal insulin, human insulin or an analog thereof.

Insulin analogs referred to here are preferably derivatives of naturally occurring insulins, namely human insulin or animal insulin, which differ from the corresponding otherwise identical naturally occurring insulin by virtue of substitution of at least one naturally occurring amino acid radical and/or addition of at least one amino acid radical and/or organic radical.

The following examples are given to illustrate the present invention. It should be understood, however, that the invention is not to be limited to the specific conditions or details described in these examples. Throughout the specification, any and all references to a publicly available documents are specifically incorporated into this patent application by reference.

EXAMPLES

The process according to the invention is illustrated in more detail below, in particular with reference to examples. Construction and mode of operation of the centrifugal dryer: The centrifugal dryer consists of a horizontally arranged centrifugal drum with a compact wall. Within the drum is a cylindrical screen cage which is firmly connected to the drum. The space between the porous surface of the screen cage and the compact surface of the drum wall is divided radially into a plurality of chambers. The rear end-surface of the drum has openings, so that during rotation of the drum either a gas (e.g. the drying gas) can be introduced into the chambers from outside, or a liquid (e.g. the mother liquor of the crystal suspension) can be drawn off from the chambers to the outside. At the front, the drum is sealed with a plunger which rotates with the drum. When the drum is at rest, the plunger can be moved in an axial direction. When the plunger is moved back, a fixed circular outlet path is opened, which is then accessible from the inside of the centrifugal drum. After the drum has been opened, the drum can be rotated slowly again (in order to discharge the dry product).

In the centrifugal dryer used in the experiments, the centrifugal drum had a diameter of 400 mm and a cylindrical wall length of 200 mm, the screen cage had a filter area of 0.25 $m^2$ and a pore size of 10 $\mu m$.

The centrifuge is charged with product (crystal suspension) axially through the hollow drive shaft as the drum is rotating (475 rpm), the filter cake (crystals) forms as a layer on the screen, and the filtrate being pressed through the screen into the chambers and from there through the base of the drum into the fixed outer space. The filtrate (crystallization mother liquor) leaves the centrifuge through the discharge port and is discarded. The filter cake is then washed with water in the same way. Subsequently, the wash water is replaced in the same way by one of the drying media given in the examples. After the filter cake has been spun dry at relatively high speed (1200 rpm), the filter cake is detached from the screen by blowing in nitrogen at a relatively low speed (6 rpm), and the detached product is converted into a fluidized bed and dried. For this drying, a pulsating stream of nitrogen is passed from outside (through the openings in the bottom of the drum) through the lower drum chambers and through the lower section of the screen into the inner space of the drum. The drying gas flows through the rotating fluidized bed of the product and leaves the drum via the upper section of the screen and the upper drum chamber. After the drying phase is complete, the plunger is moved back, thereby opening the circular outlet path. At low speed and pulsating pressure surges, the nitrogen expels the dried product into the discharge path. At the end of the discharge path, the nitrogen is separated off in a cyclone and the dry product is collected in a storage vessel.

The drying gas (nitrogen) is moistened with sterile water vapor prior to entry into the centrifugal dryer in a separate apparatus and heated to the drying temperature. The temperature and the water content in the nitrogen stream are regulated.

Example 1

In a crystallization vessel fitted with a stirrer, 1000 g of porcine insulin were crystallized from aqueous solution at pH 5.5 with addition of zinc ions. When crystallization was complete, the suspension (about 100 l) contained rhombohedral crystals having a mean particle size of 25 μm. As described above, the stirred crystal suspension was placed into the centrifugal dryer for about 30 min. The filter cake was washed with about 50 l of water and then the wash water was replaced with 70% strength aqueous ethanol (drying medium). After the filter cake had been detached from the screen, the crystals were dried in a fluidized bed. During the drying time, the drying gas was preheated to a temperature of 40° C. and adjusted to a water content of 4 g of water per 1 kg of nitrogen. After 120 min, the drying was complete and the product was emptied into a storage vessel. Analysis of the dry crystals showed a residual content of water of 5% and a residual content of ethanol of less than 0.1 %.

Example 2

In a crystallization vessel fitted with a stirrer, 1500 g of human insulin were crystallized under sterile conditions from aqueous solution at pH 5.5 with addition of zinc ions. When crystallization was complete, the suspension (about 150 l) contained rhombohedral crystals having a mean particle size of 20 μm. The centrifugal dryer was washed prior to use successively with 10% strength sodium hydroxide solution, particle-free water, 10% strength acetic acid and again with particle-free water. The centrifugal dryer was then sterilized with particle-free steam. As described above, the stirred crystal suspension was transferred to the centrifugal dryer for about 45 min. The filter cake was washed with about 50 l of water and then the wash water was replaced by 50% strength aqueous ethanol (drying medium). Both liquids had been sterilized by filtration beforehand. After the filter cake had been detached from the screen, the crystals were dried in a fluidized bed. During the drying time, the sterile-filtered drying gas was preheated to a temperature of 40° C. and adjusted to a water content of 3 g of water per 1 kg of nitrogen. After 150 min, drying was complete and the product was, as described above, emptied into a storage vessel. Analysis of the dry crystals gave a residual content of water of 4% and a residual content of ethanol of less than 0.1 %. The product was free from germs and foreign particles.

Example 3

In a crystallization vessel fitted with a stirrer, 1000 g of human insulin were crystallized from aqueous solution at pH 5.5 with addition of zinc ions. When crystallization was complete, the suspension (about 100 l) contained rhombohedral crystals having a mean particle size of 25 μm. As described above, the stirred crystal suspension was transferred to the centrifugal dryer for about 30 min. The filter cake was washed with about 50 l of water and the wash water was replaced by 30% strength aqueous ethanol (drying medium). After the filter cake had been detached from the screen, the product was dried in a fluidized bed. During the drying time, the drying gas was preheated to a temperature of 40° C. and adjusted to a water content of 5 g of water per 1 kg of nitrogen. After 120 min, drying was complete and the product was emptied into a storage vessel. Analysis of the dry crystals showed a residual content of water of 6% and a residual content of ethanol of less than 0.1%.

Example 4

In a crystallization vessel fitted with a stirrer, 1000 g of porcine insulin were crystallized from aqueous solution at pH 5.5 with addition of zinc ions. When crystallization was complete, the suspension (about 100 l) contained rhombohedral crystals having a mean particle size of 30 μm. As described above, stirred crystal suspension was transferred to the centrifugal dryer for about 30 min. The filter cake was washed with about 50 l of water and the wash water was replaced by 72% strength aqueous propanol (drying medium). After the filter cake had been detached from the screen, the product was dried in a fluidized bed. During the drying time, the drying gas was preheated to a temperature of 40° C. and adjusted to a water content of 4 g of water per 1 kg of nitrogen. After 140 min, drying was complete and the product was emptied into a storage vessel. Analysis of the dry crystals showed a residual content of water of 5 % and a residual content of propanol of less than 0.1 %.

Example 5

In a crystallization vessel fitted with a stirrer, 1500 g of di-Arg-insulin were crystallized from aqueous solution at pH 6.3 with addition of zinc ions. After crystallization was complete, the suspension (about 100 l) contained crystals having a mean particle size of 20 μm. As described above, the stirred crystal suspension was transferred to the centrifugal dryer for about 30 min. The filter cake was washed with about 50 l of water and the wash water was replaced by 25% strength aqueous propanol (drying medium). After the filter cake had been detached from the screen, the product was dried in a fluidized bed. During the drying time, the drying gas was preheated to a temperature of 40° C. and adjusted to a water content of 3 g of water per 1 kg of nitrogen. After 160 min, drying was complete and the product was emptied into a storage vessel. Analysis of the dry crystals showed a residual content of water of 6% and a residual content of propanol of less than 0%.

Example 6

In a crystallization vessel fitted with a stirrer, 1000 g of human insulin were crystallized from aqueous solution at pH 5.5 with addition of zinc ions. When crystallization was complete, the suspension (about 100 l) contained rhombohedral crystals having a mean particle size of 25 $\mu$m. As described above, the stirred crystal suspension was transferred to the centrifugal dryer for about 30 min. The filter cake was washed with about 50 l of water, and the wash water was replaced by 15% strength aqueous n-propanol (drying medium). After the filter cake had been detached from the screen, the product was dried in a fluidized bed. During the drying time, the drying gas was preheated to a temperature of 40° C. The water content in the drying gas at the start of the drying time was adjusted to 15% and was lowered to 8% during the drying time. After 120 min, the drying was complete and the product was emptied into a storage vessel. Analysis of the dry crystals showed a residual content of water of 6 % and a residual content of propanol of less than 0.1 %.

Priority application DE 19903125.8, filed Jan. 27, 1999, including the specification, claims and abstract is incorporated herein by reference in its entirety.

What is claimed is:

1. A process for drying protein crystals comprising drying an aqueous protein crystal suspension in a centrifugal dryer
   wherein the protein crystals are dried to a residual water content between 1 and 7%; and
   wherein the protein crystals are crystals of a protein selected from the group consisting of animal insulin, human insulin and an analog thereof.

2. A process for drying protein crystals, comprising:
   a) charging a centrifugal dryer with a protein crystal suspension;
   b) filtering off protein crystals from said protein crystal suspension; and
   c) bringing said protein crystals into contact with a drying medium comprising water and a nonacqueous solvent which is miscible with water in any ratio and which has a lower vapor pressure than water to a residual water content between 1 and 7%;
      wherein the protein crystals are dried to a residual water content between 1 and 7%; and
      wherein the protein crystals are crystals of a protein selected from the group consisting of animal insulin, human insulin and an analog thereof.

3. The process as claimed in claim 2, wherein the proportion of the solvent in the drying medium is from 10 to 80% inclusive.

4. The process as claimed in claim 3, wherein the proportion of the solvent in the drying medium is from 15 to 60% inclusive.

5. The process as claimed in claim 2, wherein the solvent is an alcohol or a mixture of alcohols.

6. The process as claimed in claim 5, wherein the solvent is methanol.

7. The process as claimed in claim 5, wherein the solvent is ethanol.

8. The process as claimed in claim 5, wherein the solvent is n-propanol.

9. The process as claimed in claim 5, wherein the solvent is isopropanol.

10. A process for drying protein crystals, comprising drying protein crystals in a centrifugal dryer with a drying gas that has been moistened prior to drying said crystals;
    wherein the protein crystals are dried to a residual water content between 1 and 7%; and
    wherein the protein crystals are dried to a residual water content between 1 and 7%;
    wherein the protein crystals are crystals of a protein selected from the group consisting of animal insulin, human insulin and an analog thereof.

11. The process as claimed in claim 10, wherein the drying gas is nitrogen.

12. A process for drying protein crystals, comprising:
    a) charging a centrifugal dryer with a protein crystal suspension;
    b) filtering off protein crystals from a protein crystal suspension; and
    c) drying said crystals in a fluidized beds;
       wherein the protein crystals are dried to a residual water content between 1 and 7%; and
       wherein the protein crystals are crystals of a protein selected from the group consisting of animal insulin, human insulin and an analog thereof.

13. The process as claimed in claim 3, wherein the solvent is an alcohol or a mixture of alcohols.

14. The process as claimed in claim 4, wherein the solvent is an alcohol or a mixture of alcohols.

15. The process as claimed in claim 12, wherein the protein crystals dried in the fluidized bed are dried for about 1 to 4 hours.

16. A process for drying protein crystals comprising
    (a) filtering off the crystals from an aqueous suspension to obtain a filter cake;
    (b) washing the filter cake with wash liquid;
    (c) replacing the wash liquid with a drying medium;
    (d) spin drying the filter cake;
    (e) detaching the filter cake from the filter and converting it into a fluidized bed;
    (f) drying the crystals in the fluidized bed with a stream of moistened nitrogen; and
    (g) emptying the dried crystals using a nitrogen pressure surge into a flanged container.

17. A process for drying protein crystals comprising
    (a) filtering off the crystals from an aqueous suspension to obtain a filter cake;
    (b) washing the filter cake with wash liquid;
    (c) replacing the wash liquid with a drying medium;
    (d) spin drying the filter cake;
    (e) detaching the filter cake from the filter and converting it into a fluidized bed;
    (f) drying the crystals in the fluidized bed with a stream of moistened nitrogen to a residual water content between 1 and 7%; and
    (g) emptying the dried crystals using a nitrogen pressure surge into a container.

* * * * *